US007192609B2

(12) United States Patent
Abrams et al.

(10) Patent No.: US 7,192,609 B2
(45) Date of Patent: Mar. 20, 2007

(54) USE OF RARE EARTH COMPOUNDS FOR THE PREVENTION OF KIDNEY STONE DISEASE

(75) Inventors: Michael J. Abrams, Custer, WA (US); Gary J. Bridger, Bellingham, WA (US); Simon P. Fricker, Langley (CA); Stefan R. Idzan, Surrey (CA)

(73) Assignee: Shire International Licensing B.V., Amsterdam (NL)

( * ) Notice: Subject to any disclaimer, the term of this patent is extended or adjusted under 35 U.S.C. 154(b) by 207 days.

(21) Appl. No.: 10/128,783

(22) Filed: Apr. 22, 2002

(65) Prior Publication Data

US 2002/0155168 A1    Oct. 24, 2002

Related U.S. Application Data

(60) Provisional application No. 60/285,901, filed on Apr. 23, 2001.

(51) Int. Cl.
*A61K 33/24* (2006.01)
*A61P 13/04* (2006.01)

(52) U.S. Cl. .................. 424/617; 424/715; 514/891
(58) Field of Classification Search ............. 424/617, 424/DIG. 6; 514/891, 492, 836
See application file for complete search history.

(56) References Cited

U.S. PATENT DOCUMENTS

| 5,951,958 | A | * | 9/1999 | Kimura | 423/263 |
| 5,968,976 | A | | 10/1999 | Murrer et al. | 514/492 |
| 6,200,562 | B1 | | 3/2001 | Allison et al. | 424/94.5 |
| 6,355,242 | B1 | | 3/2002 | Allison et al. | 424/93.4 |

FOREIGN PATENT DOCUMENTS

| DE | 1668562 A | 9/1971 |
| DE | 3046580 A1 * | 7/1982 |
| DE | 3213139 A1 * | 10/1983 |
| JP | 61-004528 | 1/1986 |
| JP | 62145024 | 6/1987 |
| RU | 2061040 | 5/1996 |
| WO | WO 96/30029 | 10/1996 |
| WO | WO 98/52586 | 11/1998 |
| WO | WO 99/22744 | 5/1999 |

OTHER PUBLICATIONS

PUBMED online, file MEDLINE, PMID 10421978 (Fallingborg, "Intraluminal pH of the human gastrointestinal tract", Dan. Med. Bull. (1999), vol. 43, No. 3, pp. 183-196), Abstract.*
Bailar et al., eds., Comprehensive Inorganic Chemistry (1973), pp. 82,93,94.*
STN/CAS online, file CAPLUS, Acc. No. 1968:492507, Doc. No. 69:92507 (Pajakoff, "Phosphates and phosphato complexes of rare earth metals", Monatshefte fuer Chemie (1968), vol. 99, No. 4, pp. 1400-1408), Abstract.*

Pajakoff, "Phosphates and phosphato complexes of rare earth metals", Monatshefte für Chemie (1968), vol. 99, No. 4, pp. 1400-1408.*
File MEDLINE on PUBMED online, Doc. No. 8441076 (Elton et al., A clinical prediction rule of the diagnosis of ureteral calculi in emergency departments, J. Gen. Intern. Med. (1993), vol. 8, No. 2, pp. 57-62), Abstract.*
File MEDLINE on PUBMED online, Doc. No. 2692048 (Frank et al., Urolithiasis in primary care, Prim. Care (1989), vol. 16, No. 4, pp. 967-980), Abstract.*
File MEDLINE on PUBMED online, Doc. No. 3993484 (Ebisuno et al., [Studies of urinary risk factors in urolithiasis], Hinyokika Kiyo (1985), vol. 31, No. 1, pp. 1-15), Abstract.*
File MEDLINE on PUBMED online, Doc. No. 37975 (Roberson et al., Risk factors in calcium stone disease of the urinary tract, Br. J. Urol. (1978, vol. 50, No. 7, pp. 449-454), Abstract.*
Grases et al. (1999). *International Urology and Nephrology* 31(5):591-600.
Holmes, R. et al. (2001). *Kidney International* 59:270-276.
Reginato, A.J. et al. (1989). *Semin Arthiritis Rheum* 18:198.
European Search Report, Appl. No. EP 02 76 4336, dated Jun. 2, 2004.
Absract, Dewberry et al., "*Lanthanum Carbonate An Effective Inhibitor Of Phosphate Absorption From The Intestinal Track*" Nephrology Dialysis Transplantation, Oxford University Press, GB, vol. 12, No. 9, 1997, p. A98, XP009030453.
Abstract, Hutchison, A.J. et al., "*Lanthanum Carabonate: A Novel Non-Calcaemic Phosphate Binder In Dialysis Patients*" Nephrology Dialysis Transplantation, Oxford University Press, GB, vol. 15, No. 9, Sep. 2000 (2000-09), p. A113, XP009014903.
Locatelli F. et al., "*Lanthanum Carbonate Anormed*" Current Opinion In Cardiovascular Pulmonary And Renal Investigational Drugs, Current Drugs, London, GB vol. 2, 2000, pp. 372-377, XP009030303.
Harris A.F., et al., "*The Effect Of Lanthanum Chloride And Related Compounds On Calcification*" Archives Internationales De Pharmacodynamie Et. De. Therapie, Heymans Institue Of Pharmacology, Ghent, BE, vol. 186, Aug. 1970 (1970-08), pp. 269-278, Xp000912133.
Hutchison A.J., "*Calcitriol, Lanthanum Carbonate, And Other New Phosphate Binders In The Management Of Renal Osteodystrophy*", Peritoneal Dialysis International, Pergamon Press, New York, NY, US, vol. 19, No. Suppl. 2, 1999, pp. S408-S412, XP009030319.
Y.Y. Lurji Analytical chemisty reference book:, M. "Khimia", 1989, pp. 322-323.
Russian Official Action for Appl. No. 2003133991/14(036768) dated Feb. 1, 2006.

* cited by examiner

*Primary Examiner*—Johann Richter
*Assistant Examiner*—Frank Choi
(74) *Attorney, Agent, or Firm*—Darby & Darby

(57) ABSTRACT

Conditions such as kidney stones, which are characterized by undesired absorption of oxalate from the intestinal tract are conveniently treated using nontoxic salts of rare earth metal ions.

10 Claims, 6 Drawing Sheets

USE OF RARE EARTH COMPOUNDS FOR THE PREVENTION OF KIDNEY STONE DISEASE

CROSS-REFERENCE TO RELATED APPLICATIONS

This application claims priority under 35 U.S.C. § 119(e) from Provisional Application 60/285,901 filed 23 Apr. 2001. The contents of that application are incorporated herein by reference.

TECHNICAL FIELD

This invention relates to a method of preventing or treating urolithiasis (kidney stone disease) by administering rare earth salts, e.g., Lanthanum salts, to bind dietary oxalate and preventing its absorption into the gastrointestinal tract.

BACKGROUND OF THE INVENTION

Nephrolithiasis or urolithiasis is a common disorder defined as the development of stones within the urinary tract such as the kidney stone disease. This disorder represents a serious health problem. Depending on local conditions, between 1 and 14% of the population suffers from this condition. The economic impact of urolithiasis in the U.S. was estimated to be $1.83 billion in 1993 (Grases, et al., *International Urology and Nephrology*, 31(5) pp. 591–600 (1999)). Current preventative/treatment for urolithiasis are not easy to take and not that effective, e.g., potassium citrate tablets.

Calcium oxalate is the dominant component in kidney stones. The amount of oxalate excreted in urine has a significant impact on calcium oxalate supersaturation and kidney stone formation (R. Holmes, et al., *Kidney International*, 59, pp. 270–276 (2001)). In addition, calcium oxalate is also known to be associated with arthritis (Reginato A J, Kumik B R C: "Calcium oxalate and other crystals associated with kidney disease and arthritis," *Semin Arthirtis Rheum* 18:198, 1989).

PCT publication WO 99/22744 suggests the use of aliphatic polyamines to reduce the levels of oxalate in the digestive tract. This publication suggests that the polyamines be administered orally optionally in the presence of enzymes, such as oxalate decarboxylase or oxalate oxidase which can decompose oxalate. Various forms of oral dosage are described. The contents of this publication are incorporated herein by reference.

Hydrates of lanthanum carbonate [$La_2(CO_3)_3$] are described in U.S. Pat. No. 5,968,976 and WO 96/30029 for treating hyperphosphataemia in patients with renal failure by removing elevated levels of phosphates. This treatment is especially useful in patients undergoing kidney dialysis. These compounds are particularly preferred.

There exists a need for agents that bind oxalate and thereby inhibit or prevent stone formation in the kidneys. The present invention addresses this need by using rare earth compounds to lower levels of oxalate in animals, including humans.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents.

Further, all documents referred to throughout this application are hereby incorporated in their entirety by reference herein.

DISCLOSURE OF THE INVENTION

The invention concerns methods to control, prevent, or treat subjects who are at risk for or who exhibit the symptomology of oxalate deposits in the kidneys—i.e., kidney stones, through the oral administration of rare earth salts, e.g. lanthanum salts, with high affinity oxalate binding properties.

Thus, in one aspect, the invention is directed to a method to inhibit the formation of kidney stones in a subject which method comprises administering to the gastrointestinal tract of said subject, an effective amount of a nontoxic rare earth salt, optionally in hydrated form. In typical embodiments, the rare earth salt is of the formula

$$[RE]_a[X]_b \cdot cH_2O \qquad (1)$$

wherein RE represents a rare earth cation, X represents a nontoxic anion, a and b are of suitable relative values so that a neutral salt is formed, and c has a value of 0–10.

In another aspect, the invention is directed to a method to modulate the absorption of oxalate from the gastrointestinal tract of a subject which method comprises administering the compounds of formula (1) to a subject in need of such treatment.

In another aspect, the invention is directed to the use of an optionally hydrated rare earth nontoxic salt to prepare a medicament for the treatment of subjects at risk for or exhibiting symptoms of oxalate-based kidney stones.

MODES OF CARRYING OUT THE INVENTION

Figure 1A:
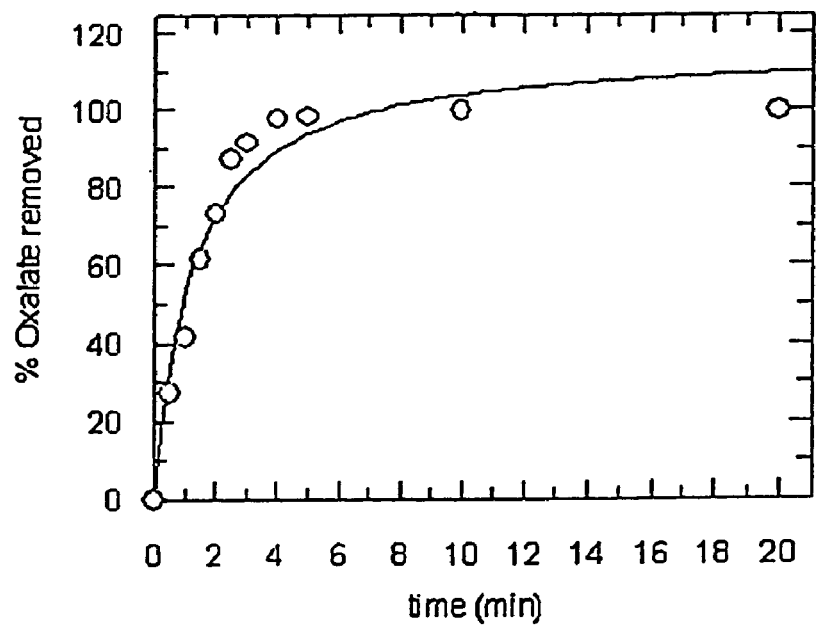
FIGS. 1A and 1B show oxalate removal by 0.1 M lanthanum carbonate hydrates, i.e., lanthanum carbonate tetrahydrate ($La_2(CO_3)_3 \cdot 4H_2O$) (FIG. 1A), and lanthanum pentahydrate ($La_2(CO_3)_3 \cdot 5H_2O$) (FIG. 1B), at pH 7 using an oxalate solution containing 0.01 M sodium oxalate and 8.5 g/L sodium chloride.

The invention provides pharmaceutical compositions using nontoxic salts of rare earth elements optionally in hydrated form. The rare earth cations are typically trivalent anions of the lanthanide series including, but not limited to, La, Ce, Pr, Nd, Sm, Eu, Gd, Tb, Dy, Ho, Er, Tm, Yb, Lu, Y and Sc, preferably La, Y and Ce. The cation is balanced by negatively charged counterions or mixtures of counterions selected from carbonate, chloride, formate, and acetate, preferably carbonate. The subscripts a and b in formula (1) above are dependent on the nature of the counterion and are selected so as to obtain a neutral salt. Waters of hydration may be present and, if present, may include as many as 10 waters of hydration, preferably less than eight, more preferably less than seven.

Preferred rare earth salts are those of yttrium, lanthanum and cerium. These rare earth salts can be counterbalanced by counterions such as acetates, chlorides or carbonates, with the carbonates being the most preferred. Also preferred are hydrated forms of these salts, especially hydrates with waters of hydration of less than 7 moles water per mole of salt, preferably 3–5 waters of hydration.

The compositions of the invention are designed for removal of oxalates from the gastrointestinal tract. Administration of these compositions is preferably to the upper digestive tract, most conveniently by oral administration. The compounds are effective over a pH range encountered in these locations which ranges from pH 2 in the stomach to pH 7 in regions downstream thereof. The compositions of the invention are not subject to degradation at high pH, and thus it is unnecessary to take special precautions, such as the supply of enteric coatings for oral administration.

The conditions characterized by kidney stones are believed to be related to inappropriate absorption of oxalate from the intestinal tract; inhibition of such absorption appears useful in controlling this condition. While not intending to be bound by any theory, applicants specifically include kidney stones among conditions that are affected by excessive oxalate absorption from the gastrointestinal tract. In addition, inappropriate absorption of oxalate from the gastrointestinal tract is itself a condition which requires remediation. The sequelae of such inappropriate absorption include the symptomology of kidney stones, but other deposits of oxalate may form in other organs as well or the levels of oxalate in the bloodstream may themselves be deleterious. Thus, any subject who exhibits levels of oxalate in the blood or serum that are higher than a normal level is also a candidate for treatment according to the method of the invention. Methods for determining oxalate levels in the diet and in the bloodstream or serum are known in the art.

Pharmaceutical compositions for oral administration according to the invention may be formulated and manufactured using methods well known in the art. Suitable diluents, carriers, excipients and other components are also well known. The compositions may be desirably be in a dosage form, to provide a single daily dose, or a number of sub-daily dosages. Conventional pharmacological methods may be used to ascertain suitable dose levels. Suitable formulations appropriate for any route of administration are known in the art and will be found, for example, in *Remington's Pharmaceutical Sciences,* latest ed., Mack Publishing Co., Easton, Pa. Suitable forms for oral administration include solid forms for oral administration include solid forms such as tablets, capsules and dragees and liquid forms such as suspensions or syrups. In addition to diluents and carriers, it is conventional in the formulation of oral preparations to include non-active ingredients such as thickeners, taste-improving components and coloring agents. The compound in the pharmaceutical composition may also be coated or treated to provide delayed-release forms. Preferably, the required daily dosage is given in tablet form, e.g., chewable tablet form.

By "treat" is meant either to ameliorate a condition that already exists or to inhibit the acquisition of a condition or further accretion of a condition that does not yet exist or that exists in a form that has a potential for progressing to more undesirable levels. Thus, by "treat" or "treatment" includes both therapeutic and prophylactic uses.

Individuals who may be treated by the methods of the invention include those who exhibit symptomology of kidney stones, have confirmed diagnosis of kidney stones, or are suspected by virtue of alternative symptoms of this condition. Also suitable subjects for the methods of the invention are those who would benefit from the removal of oxalate from the intestines generally; individuals with diets having high levels of oxalate intake, for example, would also be included. Further, individuals whose family history indicates a risk for inappropriate absorption of oxalate from the intestines would also be benefited. The treating practitioner would be in a position, based on tools of diagnosis available in the field, to identify those individuals who would benefit from modulation of the absorption of oxalate from the gastrointestinal tract.

The compositions to be administered may include additional active ingredients such as the aliphatic polyamines disclosed as described above in WO 99/22744 and any other medications compatible with the rare earth salts which may be intended for treatment of other conditions also experienced by the subject. While not intending to be bound by any theory, it is believed that the rare earth compounds of the invention form insoluble materials with the dietary oxalate and effect the excretion of the insolubilized oxalate from the subject without providing the opportunity of the oxalate to enter the urinary system.

Having now generally described the invention, the same will be more readily understood through reference to the following examples which are provided by way of illustration, and are not intended to be limiting of the present invention, unless specified.

EXAMPLES

Example 1

Oxalate Binding Assay

In order to assess removal of oxalate from a stock solution by lanthanum carbonate, an oxalate binding assay was developed. The assay was based on the phosphate binding assay previously developed for assessing removal of phosphate from a stock solution by lanthanum carbonate (U.S. Pat. No. 5,968,976). Further, the buffer conditions were designed to mimic the conditions present in the stomach and in the small intestine. Briefly, 50 mL of a stock sodium oxalate solution containing 8.5 g/L sodium chloride was adjusted to the desired pH using 5N HCl and the Mettler-Toledo DL58 autotitrator. Various combinations of oxalate and lanthanum carbonate concentrations were tested to determine which would maximize oxalate removal. Prior to the addition of the desired amount of lanthanum carbonate, a 2 mL sample was taken to act as a zero time point sample. The volume of buffer was made up to 50 mL again by adding 2 mL of stock oxalate buffer back to the pH adjusted buffer and the lanthanum carbonate was added. A timer was started and 2 mL samples were removed at predetermined time intervals over twenty minutes and filtered through a 0.02 μm syringe filter (Whatman Anotop 10 #6809 1002). Filtered samples were analyzed for oxalate using a modified version of Sigma Diagnostics' Oxalate Assay Kit (Sigma #591-D) and an oxalate standard curve. Modifications of the oxalate assay included assaying only 25 μL of appropriately diluted, filtered sample instead of 50 μL, as well as using only 0.5 mL of Oxalate Reagent A (Sigma #591-10) and only 50 μL of Oxalate Reagent B (Sigma #591-2). In addition, samples were assayed at 590 nm in a Falcon 96-well microplate using the Molecular Devices Spectramax 190 plate reader.

Figure 1B:
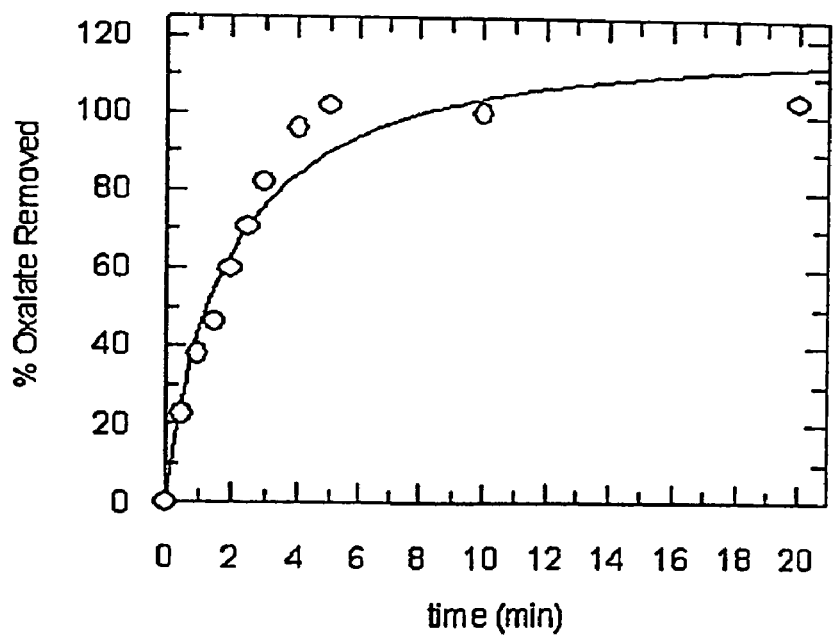

With respect to this assay, shown in FIG. 1, the oxalate binding was strongest when 50 mL of oxalate buffer containing 0.01 M sodium oxalate and 8.5 g/L sodium chloride was adjusted to pH 7 and lanthanum carbonate was added at a concentration of 0.1 M (2.74 g $La_2(CO_3)_3.4H_2O$ (FIG. 1A) or 2.65 g $La_2(CO_3)_3.5H_2O$) (FIG. 1B). In order to maximize the accuracy of the results, the filtered samples were assayed at a 1/20 dilution. FIGS. 1A and 1B show that different hydrated forms of lanthanum carbonate, lanthanum carbonate tetrahydrate and lanthanum carbonate pentahydrate, can effectively bind oxalate pH 7.0.

Figure 2:
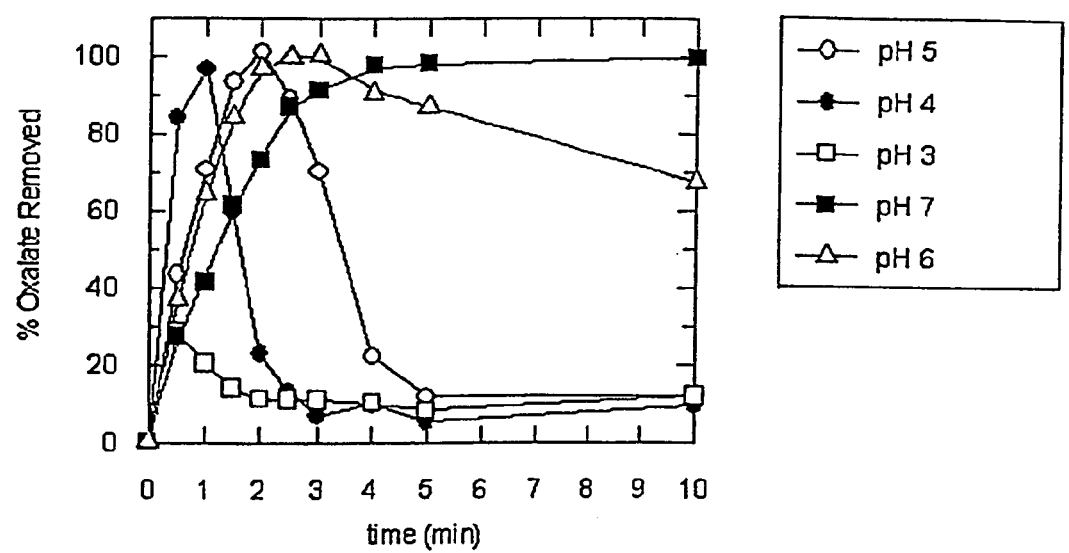
FIG. 2 shows a comparison of oxalate binding by lanthanum carbonate tetrahydrate at pH 3 to pH 7.

The procedure described above was repeated at various pH's in the range of 3–7. The results are shown in FIG. 2. These results demonstrate that lanthanum tetrahydrate can bind oxalate in this pH range (3–7) with preferential binding at pH 6–7.

Example 2

Competitive Binding of Oxalate and Phosphate Using Lanthanum Carbonate

Having found an appropriate concentration combination of oxalate and lanthanum carbonate, competitive binding of oxalate and phosphate by lanthanum carbonate was also explored. The competitive binding assay was based on the phosphate binding assay previously developed for assessing removal of phosphate from a stock solution by lanthanum carbonate (U.S. Pat. No. 5,968,976) as well as the results from the current studies using oxalate. Briefly, a stock solution containing 0.1M anhydrous disodium phosphate, 0.01M sodium oxalate, and 8.5 g/L sodium chloride was prepared. Then, 50 ml of this stock solution was adjusted to either pH 3 or pH 7 using 5N and a Mettler-Toledo DL58 autotitrator. Just prior to the addition of lanthanum carbonate, a 2 ml sample was taken to act as a zero time point sample. The volume of buffer was made up to 50 ml again by adding 2 mL of stock oxalate/phosphate buffer back to the pH adjusted buffer and the lanthanum carbonate was added. Lanthanum carbonate was added so that a concentration of 0.1M was present in the 50 mL of either pH 3 or pH 7 phosphate/oxalate buffer. A timer was started and 2 mL samples were removed at pre-determined time intervals over twenty minutes and filtered through a 0.02 µm syringe filter (Whatman Anotop 10#6809 1002). As shown in FIG. 3, filtered samples were then analyzed for the removal of both oxalate and phosphate. Oxalate removal was assessed by assaying 1/20 dilutions of each sample using a modified version of Sigma Diagnostics' Oxalate Assya Kit (Sigma #591 D) and an oxalate standard curve. Modifications of the oxalate assay included assaying only 25 µL of appropriately diluted, filtered sample instead of 50 µL, as well as using only 0.5 ml of Oxalate Reagent A (Sigma #591-10) and only 50 µL of Oxalate Reagent B (Sigma #591-2). In addition, samples were assayed at 590 nm in a Falcon 96-well microplate using the Molecular Devices Spectramax 190 plate reader. Phosphate removal was assessed by assaying 1/500 dilutions of each sample using the Sigma Diagnostics' Inorganic Phosphorus Assay Kit (Sigma #670-C) and an inorganic phosphorus standard curve. The phosphorus assay was performed as outlined in Sigma Procedure #670.

Figure 3A:
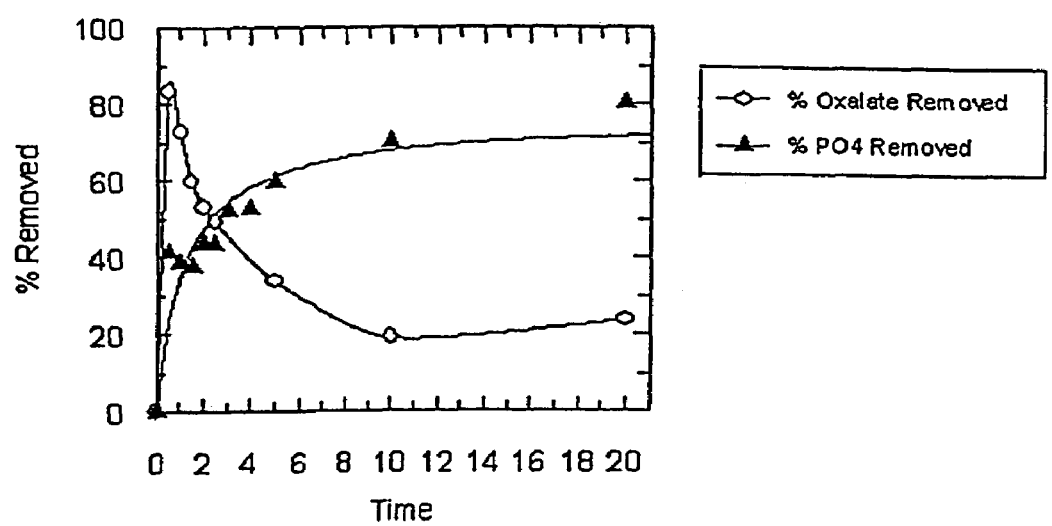
FIGS. 3A and 3B show competitive binding of a 0.01 M oxalate and 0.1 M phosphate solution using 0.1 M lanthanum carbonate at pH 3 (FIG. 3A) and pH 7 (FIG. 3B).
Figure 3B:
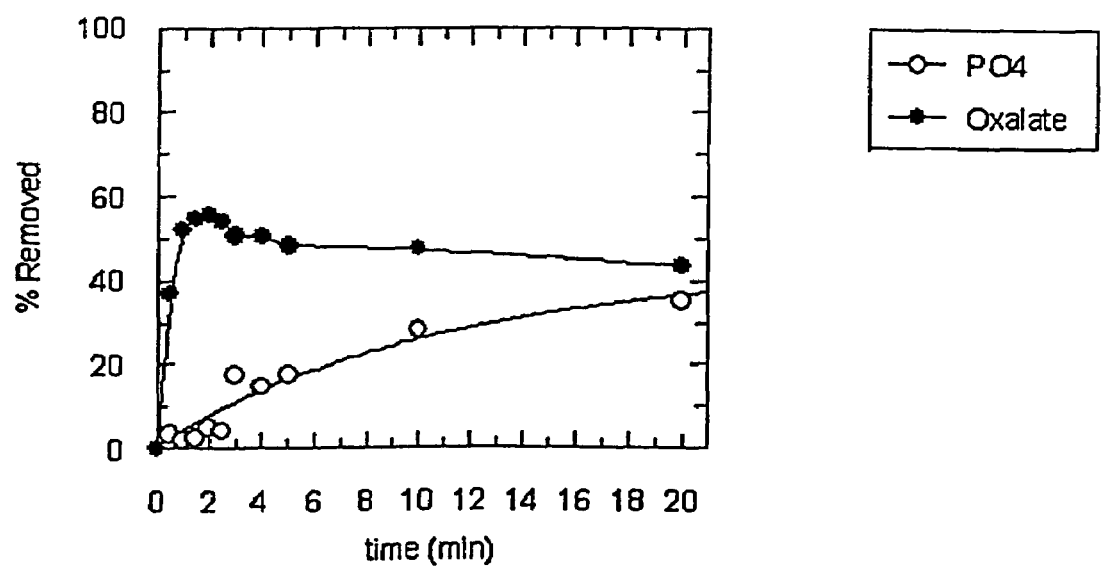

FIGS. 3A and 3B show the results of competitive binding assay for oxalate solutions as compared to phosphate solutions. One of the major dietary components that could compete for oxalate is phosphate. Dietary phosphate levels are of the order of 10 times greater than oxalate. Dietary phosphate intake is between 800–1500 mg/day and approximately 300 mg P/meal. Dietary oxalate intake is approximately 100 mg/day. The results in FIG. 3 examine the potential competitive effect of phosphate on oxalate binding by lanthanum carbonate. In the presence of a 10-fold excess of phosphate lanthanum carbonate pentahydrate was shown to preferentially bind oxalate over phosphate at pH 7.0, (FIG. 3B) the optimum pH at which lanthanum carbonate was shown to bind oxalate (FIG. 2). Preferential binding of phosphate was demonstrated at pH 3.0 (FIG. 3A). This result therefore demonstrates that even in the presence of 10-fold excess phosphate lanthanum carbonate can still effectively bind oxalate, and the different pH optima for phosphate and oxalate binding further indicates that phosphate will not interfere with oxalate binding.

Example 3

Oxalate Binding by Additional Rare Earth Compounds

Figure 4A:
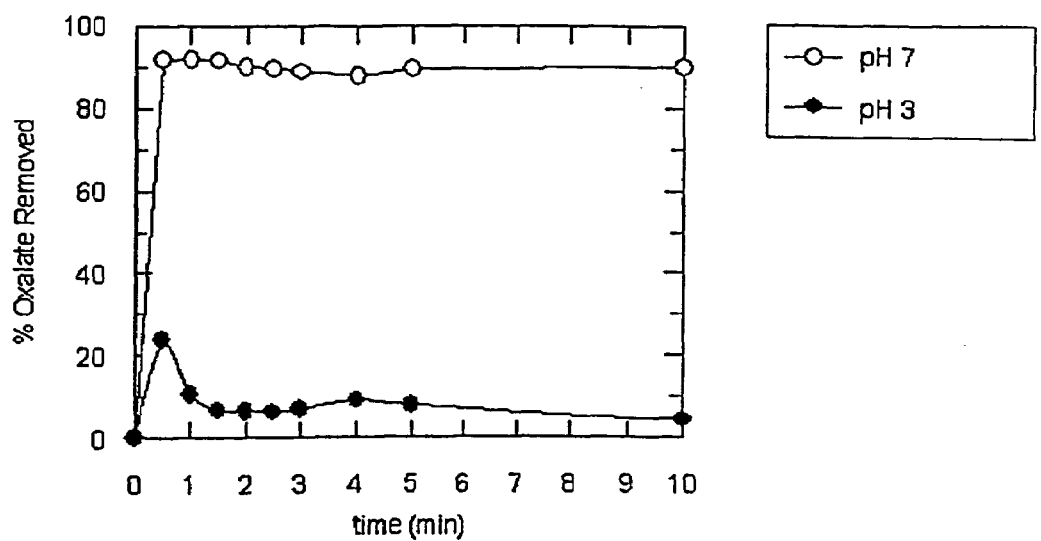
FIGS. 4A and 4B show oxalate binding by yttrium carbonate [$Y_2(CO_3)_3 \cdot 3H_2O$] (FIG. 4A) and cerium carbonate [$Ce_2(CO_3)_3 \cdot XH_2O$] (FIG. 4B) (supplied by Aldrich) at pH 3 and pH 7.
Figure 4B:
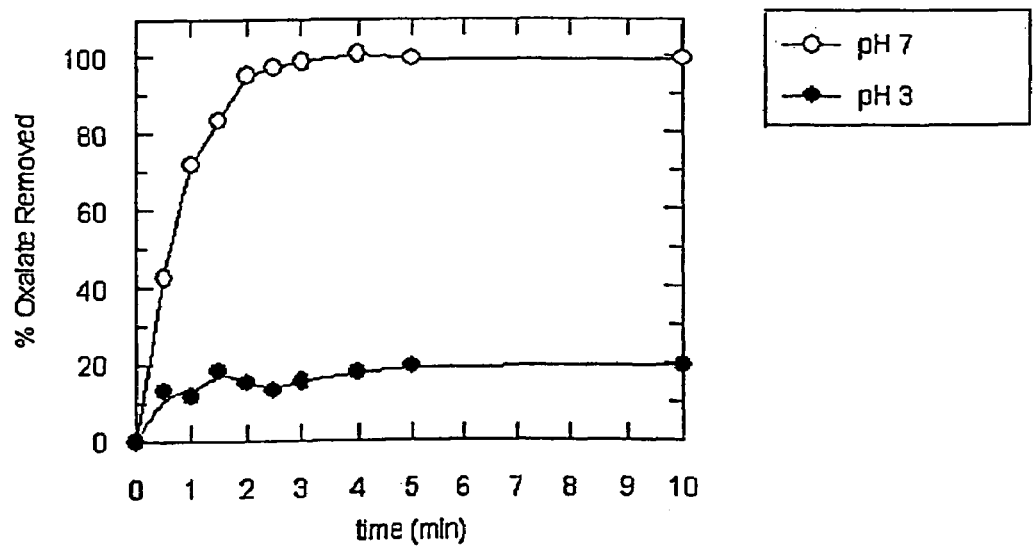

These data demonstrate that other lanthanide salts can effectively bind oxalate. Yttrium carbonate and cerium carbonate were tested for the ability to bind oxalate as described in Example 1. As shown in FIG. 4, both 0.1 M yttrium carbonate (FIG. 4A) and 0.1 M cerium carbonate (FIG. 4B) were as effective as 0.1 M lanthanum carbonate at binding oxalate at pH 7, but less effective at pH 3.

Figure 5:
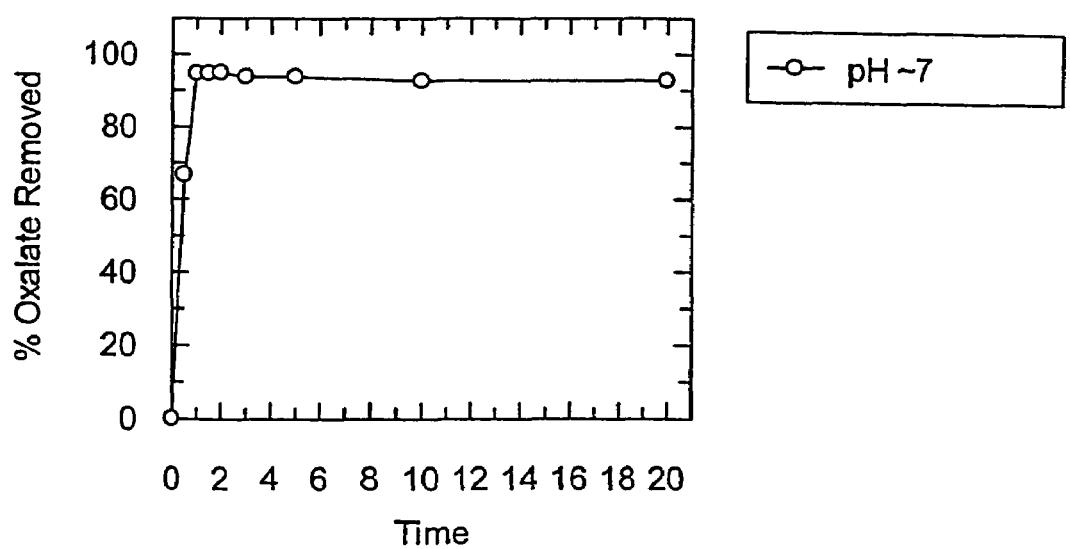
FIG. 5 shows oxalate removal by lanthanum chloride at pH 7.

Lanthanum, yttrium and cerium rare earth chlorides, and acetates were also assayed at pH 7 for oxalate binding using the assay procedure of Example 1. The assay was similar to that outlined in Example 1 except that after the oxalate solution was adjusted to the desired pH using 5N HCl, the pH was maintained with 1N NaOH. This was necessary since both the chloride compounds as well as the acetate compounds drop the pH of the solution significantly upon there addition. As shown in FIG. 5, at pH 7 lanthanum chloride binds oxalate quite rapidly.

Similar results were obtained for cerium chloride as well as yttrium chloride. Rare earth acetates were also assayed at both pH 3 and pH 7, however, the results indicated that none of the rare earth acetates bound oxalate sufficiently well at either pH.

Example 4

Simulation of pH Transition in the Digestive Tract

In order to simulate the passing of lanthanum oxalate through the digestive system, a final experiment was designed which would study both oxalate and phosphate removal as the pH changed from pH 3 (i.e. stomach pH) to pH 7 (i.e. approximate intestinal pH). This experiment was performed to address the feasibility of lanthanum carbonate as an oxalate binder in the gut where there is both a high competing phosphate level and a pH transition from pH 3 in the stomach to pH 7 in the small intestine. Previous results had shown that (1) the oxalate binding was optimal at around neutral pH, (2) lanthanum carbonate could successfully compete for phosphate at pH 7, and (3) that binding ability was lower at pH 3.

Figure 6:
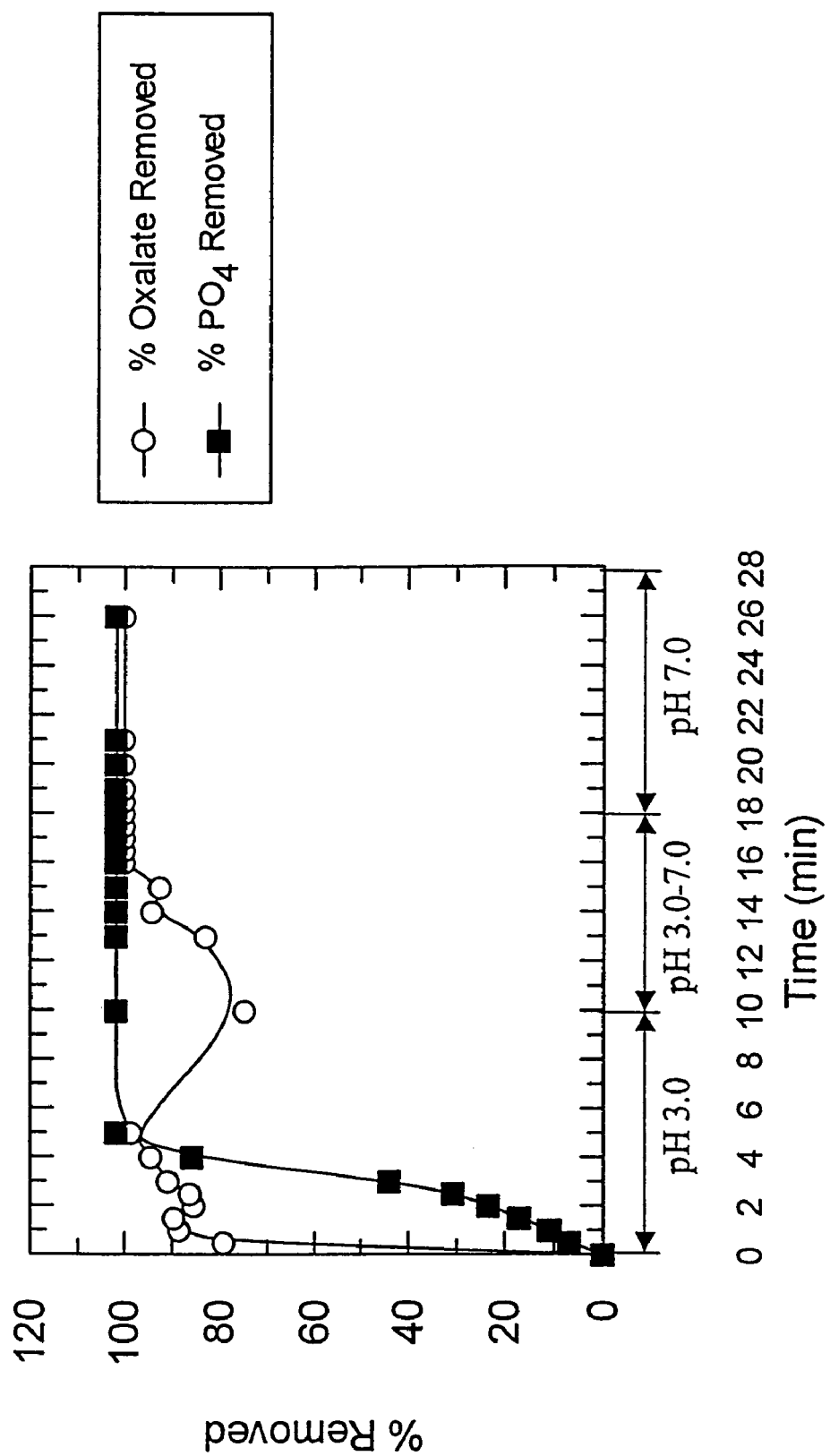
FIG. 6 shows removal of oxalate and phosphate by lanthanum carbonate as pH changes from pH 3 to pH 7.

To start, 0.1M lanthanum carbonate was added to a solution containing 0.1M phosphate and 0.01M oxalate at pH 3. Removal of both oxalate and phosphate were monitored for ten minutes. After ten minutes, the pH was gradually increased to pH 7. Samples were taken at pH 4, 5, 6, and 7 in order to assess changes in the amount of oxalate and phosphate present in the solution. As shown in FIG. 6, upon achieving pH 7, the solution was monitored for an additional ten minutes. The results demonstrate that lanthanum carbonate can successfully bind oxalate in the presence of excess phosphate under the pH conditions found during the transition from the stomach to the small intestine.

The invention claimed is:

1. A method of treating a condition characterized by unwanted absorption of oxalate from the gastrointestinal tract of a subject diagnosed as exhibiting said unwanted absorption which method comprises administering orally to said subject a hydrated lanthanum carbonate of the formula $[La]_2[CO_3]_3 \cdot cH_2O$, wherein c is 0–10, in an amount effective to inhibit the absorption of oxalate from the gastrointestinal tract, wherein the lanthanum carbonate is effective at binding oxalate in the presence of excess phosphate as the lanthanum carbonate passes through the stomach and the small intestine of the subject, the lanthanum carbonate preferentially binding the oxalate over the phosphate as the lanthanum carbonate passes through the small intestine.

2. The method of claim, 1 wherein the condition is diagnosed by the presence of oxalate kidney stones.

3. The method of claim 1 wherein said subject diagnosed is at risk for oxalate kidney stones.

4. The method of claim 1 wherein said lanthanum carbonate is hydrated.

5. The method of claim 4 wherein c is 3–5.

6. The method of claim 5 wherein c is 4 or 5.

7. The method of claim 1, further comprising the removal of oxalates from the gastrointestinal tract of the subject, where the subject is at risk for or exhibits symptoms of oxalate-based kidney stones.

8. The method of claim 1, wherein the subject is a human.

9. The method of claim 1, wherein the phosphate is present in the gastrointestinal tract in an amount up to a 10-fold excess of the oxalate.

10. The method of claim 1, wherein the treatment is applicable to subjects exhibiting symptomology of kidney stones, having confirmed diagnoses of kidney stones, or who are suspect by virtue of alternative symptoms of having kidney stones.

* * * * *

UNITED STATES PATENT AND TRADEMARK OFFICE
CERTIFICATE OF CORRECTION

PATENT NO. : 7,192,609 B2 Page 1 of 1
APPLICATION NO. : 10/128783
DATED : March 20, 2007
INVENTOR(S) : Abrams et al.

It is certified that error appears in the above-identified patent and that said Letters Patent is hereby corrected as shown below:

On The Title Page

[*] Notice: Subject to any disclaimer, the term of this patent is extended or adjusted under 35 USC 154(b) by (207) days Delete the phrase "by 207" and insert -- by 154 days--

Signed and Sealed this

Thirteenth Day of November, 2007

JON W. DUDAS
*Director of the United States Patent and Trademark Office*